United States Patent [19]

Asano et al.

[11] 4,202,885

[45] May 13, 1980

[54] PROCESS FOR THE PREPARATION OF ANTI-TRANSPLANTED SARCOMA 180 TUMORIGENIC SUBSTANCES

[75] Inventors: Kiro Asano, Kukizaki; Tsuyoshi Saito; Hiromitsu Tanaka, both of Tokyo; Satoru Enomoto, Fujisawa, all of Japan

[73] Assignee: Kureha Kagaku Kogyo Kabushiki Kaisha, Tokyo, Japan

[21] Appl. No.: 749,621

[22] Filed: Dec. 13, 1976

[30] Foreign Application Priority Data

Dec. 18, 1975 [JP] Japan .................................. 50-150114

[51] Int. Cl.$^2$ .......................... A61K 35/12; C07H 1/08
[52] U.S. Cl. ........................................... 424/95; 536/1

[58] Field of Search ................................ 424/95; 536/1

[56] References Cited

FOREIGN PATENT DOCUMENTS 1331513  9/1973  United Kingdom ...................... 424/195

Primary Examiner—Jerome D. Goldberg
Attorney, Agent, or Firm—Stevens, Davis, Miller & Mosher

[57] ABSTRACT

Extraction of a fungus of the class Basidiomycetes belonging to the Coriolus genus with an aqueous solvent under pressure and at a temperature of 120° C. to 200° C. gives an anti-transplanted sarcoma 180 tumorigenic substance in a high yield.

4 Claims, No Drawings

PROCESS FOR THE PREPARATION OF ANTI-TRANSPLANTED SARCOMA 180 TUMORIGENIC SUBSTANCES

FIELD OF THE INVENTION

This invention relates to a process for advantageously preparing anti-transplanted sarcoma 180 tumorigenic substances by extracting a fungus of the class Basidiomycetes belonging to the Coriolus genus with an aqueous solvent under certain specified conditions.

BACKGROUND OF THE INVENTION

It is well known that antitumorigenic substances composed of polysaccharides can be prepared by refining the extract obtained from extraction of the Basidiomycetes fungus with an aqueous solvent under normal pressure. The known process, however, has a serious disadvantage that the extraction method employed therein is intolerably poor in efficiency of extraction of the active components. The low extracting efficiency results in a considerable loss of the active components left over in great quantity in the extraction residue. This is quite undesirable not only from the viewpoint of productivity of the antitumorigenic substances but also from the viewpoint of loss of the valuable materials and of disposal of waste materials.

BRIEF SUMMARY OF THE INVENTION

In the course of study directed to eliminating the above-mentioned problems in preparation of anti-transplanted sarcoma 180 tumorigenic substances from extraction of the fungus of the class Basidiomycetes with an aqueous solvent, we have found that a nitrogen-containing polysaccharide having an excellent antitumorigenic activity can be obtained in a high yield when a Basidiomycetes fungus belonging to the Coriolus genus is extracted with an aqueous solvent under pressure and at a temperature within the range of 120° to 200° C.

The term "Basidiomycete fungus (or simply Basidiomycetes) belonging to the Coriolus genus" is used here to refer to the fungi of the class Basidiomycetes which belong to the Coriolus genus of the Polyporaceae family in the plant classification, and such Basidiomycetes are known to include, for example, the following: *Coriolus versicolor* (Fr.) Quél, *Coriolus hirsutus* (Fr.) Quél, *Coriolus consors* (Besh.) Imaz, *Coriolus conchifer* (Schw.) Pat, *Coriolus pubescens* (Fr.) Quél, *Coriolus pargamenus* (Fr.) Pat and *Coriolus biformis* (Klotz.) Pat. (See COLOURED ILLUSTRATIONS OF FUNGI OF JAPAN by Rokuya Imazeki and Tsuguo Hongo, Vols. I, 1974 and II, 1975).

Also the term "Basidiomycetes belonging to the Coriolus genus" used herein is to be interpreted as meaning the mycelia and fruit bodies of that fungus genus.

Thus, the principal object of this invention is to provide a process of preparing substances with excellent antitumorigenic activites in a high yield by means of extraction from the myclia and/or fruit bodies of the Basidiomycetes belonging to the Coriolus genus.

Other objects of this invention will become apparent from a consideration of the following detailed description of the invention.

DETAILED DESCRIPTION OF THE INVENTION

The feature of this invention resides in that the Basidiomycetes belonging to the Coriolus genus are extracted with an aqueous solvent under pressure and at a temperature within the range of 120° to 200° C. to obtain an antitumorigenic nitrogen-containing polysaccharide.

It has been generally thought that if the Basidiomycetes are extracted at a high temperature, such as at 120° to 200° C., the active ingredients of the fungus are decomposed, so that although it might be possible to increase the overall extraction rate, it is hardly possible to improve the yield of the desired anti-transplanted sarcoma 180 tumorigenic substances.

However, the present invention resides in the discovery that the desired anti-transplanted sarcoma 180 tumorigenic substance can be obtained in a high yield, quite contrary to the general belief, if the extraction in the above-mentioned temperature range is carried out under pressure.

For performing the extraction under pressure according to the present invention, the starting material, the mycelia and/or fruit bodies of the Basidiomycetes belonging to the Coriolus genus are put into a pressure vessel, such as for example a batch type autoclave or a flow type tubular extractor, together with an aqueous solvent, and the material is extracted therein at a temperature of from 120° to 200° C. The pressure applied in this treatment is on a level equivalent to the total vapor pressure of the aqueous solvent contained in the vessel. Usually, it is not higher than 20 kg/cm$^2$, preferably less than 16 kg/cm$^2$, but should not be lower than 1.8 kg/cm$^2$. The extraction time may be suitably adjusted depending on the temperature, but usually it is preferably within the range of 5 to 360 minutes. That is, an appropriate extraction time is selected from within the above-mentioned range in accordance with the temperature which is within the range of 120° to 200° C. If the extraction temperature is lower than 120° C., no satisfactory extraction effect is provided, while if such temperature exceeds 200° C., decomposition of the active principle may take place to render the process impractical. It should be also noted that an extraction time of shorter than 5 minutes results in poor extraction, while an extraction period of longer than 360 minutes may cause decomposition of the active principle.

In practice of the process of this invention, the extracting operation may be carried out repeatedly under the above-mentioned conditions, or the starting material (Basidiomycetes) may be immersed in an aqueous solvent at a temperature of lower than 100° C. previous to the extracting operation, or otherwise the obtained extract may be washed with an aqueous solvent at a temperature of less than 100° C. after extraction.

The aqueous solvent used in this invention may be of the type commonly used in the known methods, such as, for example, pure water, aqueous acid or alkaline solution, aqueous urea solution or aminoacid solution. Such aqueous solvent is usually used in the ratio of from five times to one hundred times, preferably, from ten times to fifty times (by weight) the amount of the starting material. The most preferred aqueous solvent for use in this invention is water or a dilute alkali solution of less than 1 N.

The thus obtained extract is then refined by way of ultrafiltration, salting-out, dialysis, reverse osmosis or other means, which may be used either singly or in combination, to remove the low molecular weight substances (those with molecular weight of less than 5,000) in the extract. This refining treatment gives a nitrogen-containing polysaccharide having an excellent antitumorigenic activity.

The substances composed of the nitrogen-containing polysaccharides obtained according to the process of this invention show excellent antitumorigenic activity, with particularly high inhibitory effect against Sarcoma-180 solid cancer, not only in intraperitoneal administration but also in oral administration to mice. This means that the nitrogen containing polysaccharides of this invention can provide a splendid anti-cancer medicine, and such effect has been confirmed by many experiments. The use of the substances obtained according to this invention is not limited to the oral applications for producing the anti-transplanted sarcoma 180 tumorigenic activities; they also stimulate immune responses.

As described above, according to the process of this invention, the nitrogen-containing polysaccharides which produce an excellent anti-transplanted sarcoma 180 tumorigenic activity not only in intraperitoneal administration but also in oral administration, in addition to the other efficacies such as mentioned above, can be obtained in a high yield and with a relatively simple process as described in the following embodiments of the invention. Thus, the present invention offers a great technical contribution to the industrial manufacture of the anti-cancer substances from Basidiomycetes.

Now the present invention is described in further detail by way of some preferred embodiments.

EXAMPLE 1

Mycelia of Coriolus versicolor (Fr.) Quel obtained by artificial culture were dried to 10% water content and divided into five portions, and then each portion was mixed with 12.5 times as much (by weight) water and fed into an autoclave, followed by extraction therein under the extracting conditions shown in Table 2 below. The extract obtained from each portion was then filtered to fractionate the extract solution alone, and the obtained extract solution was subjected to a 72-hour current water dialysis at 5° C. by using by using a dialysis tube (Visking Tube Mfd. by Union Carbide Corp.) according to a normal method. This dialytic treatment eliminates the low molecular weight substances (those with molecular weight of lower than 5,000) in the extract. The dialyzate solution was further concentrated to obtain a liver-brown powder with a water content of 7%. This powdery material had an average molecular weight of greater than 10,000, and the results of the elemental analysis and various color reaction tests shown in Table 1 below verified that this material is a nitrogen-containing polysaccharide.

Table 1

| Color reaction | Color reaction tests Color | Remarks |
| --- | --- | --- |
| α-naphthol-sulfuric acid reaction (Molish reaction) | Purple | Saccharide was confirmed. |
| Indole-sulfuric acid reaction (Dish reaction) | Brown | " |
| Anthrone-sulfuric acid reaction | Greenish blue | " |
| Phenol-sulfuric acid reaction | Brown | " |
| Tryptophane-sulfuric acid reaction | Purplish brown | " |
| Lowry-Folin process | Blue | Peptide bond was confirmed. |
| Ninhydrin reaction after hydrochloric acid hydrolysis | Purplish blue | α-aminoacid was confirmed. |

It will be understood from the results of the above tests that the products of this invention are polysaccharides containing primarily peptide-bonded nitrogen.

In order to determine the anti-transplanted sarcoma 180 tumorigenic effect of the nitrogen-containing polysaccharides obtained according to the present invention, the following test was carried out.

TESTING METHOD

Sarcoma-180 tumor cells were transplanted into the abdominal cavities of mice, and seven days later (after sufficient multiplication of the cells), $10^6$ pieces of the cells were further transplanted to the subcutaneous areas of the axillae of other group of mice to develop solid tumors. Intraperitoneal administration of the substance of this invention was started from 24th hour after transplantation. The substance was administered 10 times, once a day but every other day, at the dose of 10 mg/kg per administration, for the total amount of 0.2 ml/20 g (mouse body weight). On 25th day after transplantation, the tumor in each mouse was enucleated and its weight was measured. The tumor growth inhibitory performance of the substance of this invention was calculated from the average weight of tumors in the group of mice to which the substance of this invention had been administered and the average weight of tumors in the control.

The results of the measurements are shown in Table 2 below in a summarized form. The particulars for preparation of the respective specimens used in this test, that is, amount of aqueous solvent (water) used, extraction temperature and time, extraction rate, selectivity and yield, are also shown in Table 2.

Table 2

| Specimen No. | Water amount (wt ratio to fungus) | Temp. (°C.) | Time (min) | P. (kg/cm$^2$) | Extraction rate (%) | Selectivity (%) | Yield against fungus (%) | Inhibition against Sarcoma-180 (%) | Nitrogen content (%) |
| --- | --- | --- | --- | --- | --- | --- | --- | --- | --- |
| 1 | 12.5 | 120 | 360 | 2.0 | 34.5 | 52.2 | 18.1 | 89.9 | 0.71 |
| 2 | 12.5 | 150 | 60 | 5.0 | 51.5 | 52.5 | 27.1 | 87.9 | 0.72 |
| 3 | 12.5 | 160 | 60 | 6.3 | 62.0 | 68.4 | 42.4 | 91.0 | 0.72 |
| 4 | 12.5 | 165 | 30 | 7.2 | 68.8 | 59.0 | 40.6 | 93.0 | 0.73 |
| 5 | 12.5 | 180 | 20 | 10.2 | 80.6 | 70.6 | 57.0 | 94.9 | 0.73 |

Comparative

Table 2-continued

| Specimen No. | Water amount (wt ratio to fungus) | Temp. (°C.) | Time (min) | P. (kg/cm$^2$) | Extraction rate (%) | Selectivity (%) | Yield against fungus (%) | Inhibition against Sarcoma-180 (%) | Nitrogen content (%) |
| --- | --- | --- | --- | --- | --- | --- | --- | --- | --- |
| Example | 12.5 | 98 | 360 | | 21.6 | 47.9 | 10.4 | 89.8 | 0.71 |

(notes)
[1]Comparative Example is a specimen prepared by using the same Basidiomycete as Specimens 1 to 5 according to this invention but by extracting under normal pressure according to a conventional method.
[2]"Extraction rate" is the dissolved rate of fungus used as starting material, which is expressed by weight (%).
[3]"Selectivity" is the percent yield of the nitrogen-containing polysaccharides with molecular weight of greater than 10,000, obtained from the extract.
[4]"Yield against fungus" is the percent yield, as against the total fungus feed, of the nitrogen-containing polysaccharides with molecular weight of greater than 10,000.

It will be understood from the results shown in Table 2 that, in the tests conducted on the mice which had been subcutaneously transplanted with Sarcoma-180 tumor cells, each of the nitrogen-containing polysaccharides obtained under the extraction conditions according to this invention exhibits an equal or higher antitumorigenic activity in comparison with the similar preparations obtained under the conventional extraction conditions, and it is to be particularly noted that the yield against the amount of fungus used is markedly improved.

EXAMPLE 2

The mycelia of the same Basidiomycetes as used in Example 1 were divided into eight groups, and each group was fed into an autoclave together with 12.5 times as much (by weight of the mycelia) of an alkaline or substantially neutral aqueous solution shown in Table 3 below, followed by extraction under the pressure and temperature conditions also shown in Table 3. After extraction, the material in the autoclave was neutralized and filtered to fractionate the extract solution by separating the insolubles as extraction residue. This extract solution was subjected to a dialysis treatment according to the procedure described in Example 1 to recover the substances with average molecular weight of greater than 10,000. When these substances were tested by various color reactions shown in Table 1, it was confirmed that they are nitrogen-containing polysaccharides. In order to determine the anti-transplanted Sarcoma 180 tumorigenic activity of the thus obtained nitrogen-containing polysaccharides, Specimens 1 to 8 of these substances were administered to the mice who had been subcutaneously transplanted with Sarcoma-180. The results showed that these substances produce equal or higher anti-transplanted sarcoma 180 tumorigenic effect as compared with the nitrogen-containing polysaccharides obtained according to the conventional hot water extraction method under normal pressure.

Table 3

| Specimen No. | Solvent | Temp. (°C.) | Time (min) | P. (kg/cm$^2$) | Extraction rate (%) | Selectivity (%) | Yield against fungus (%) | Inhibition against Sarcoma-180 (%) | Nitrogen content (%) |
| --- | --- | --- | --- | --- | --- | --- | --- | --- | --- |
| 1 | 0.1N-NaHCO$_3$ | 120 | 60 | 2.0 | 40.0 | 58.0 | 21.2 | 92 | 4.92 |
| 2 | 2N-NaHCO$_3$ | 160 | 60 | 6.3 | 74.4 | 36.6 | 27.0 | 90 | 4.12 |
| 3 | 0.1N-NaHCO$_3$ | 160 | 60 | 6.3 | 50.7 | 46.8 | 24.6 | 92 | 3.65 |
| 4 | 0.1N-NaHCO$_3$ | 180 | 20 | 10.2 | 57.4 | 51.9 | 29.8 | 92 | 2.12 |
| 5 | 0.1N-NaHCO$_3$ | 200 | 20 | 15.5 | 84.3 | 50.3 | 42.4 | 98 | 1.25 |
| 6 | 0.1N-NaOH | 180 | 60 | 10.2 | 72.6 | 50.0 | 38.1 | 91 | 2.39 |
| 7 | 14% NH$_4$OH | 180 | 180 | 18.0 | 68.9 | 30.5 | 21.0 | 94 | 5.29 |
| 8 | 1% L-glutamine | 200 | 10 | 15.5 | 85.1 | 55.1 | 46.9 | 92 | 3.42 |
| Comparative Example | 0.1N-NaOH | 98 | 60 | | 22.3 | 38.1 | 8.5 | 90 | 4.91 |

(Notes)
[1]Comparative Example is a specimen prepared by using the same Basidiomycetes as Specimens 1 to 8 of this invention according to the conventional normal-pressure hot-water extraction method.
[2]The other headings are as explained in connection with Table 2.

What is claimed is:

1. A process for preparing a nitrogen-containing polysaccharide comprising:
    contacting a fungus of the genus Coriolus of the Polyporaceae family of class Basidiomycetes selected from the group consisting of *Coriolus biformis, Coriolus conchifer, Coriolus consors, Coriolus hirsutus, Coriolus pargamenus, Coriolus pubescens* and *Coriolus versicolor* with an aqueous solvent under pressure at a temperature within the range of 150° to 200° C. to obtain an extract containing the nitrogen-containing polysaccharide;
    refining said abstract to remove substances having a molecular weight less than 5,000;
    separating nitrogen-containing polysaccharide from said extract.
2. The process according to claim 1, wherein said extraction is carried out under pressure within the range of 5 to 20 kg/cm$^2$.
3. The process according to claim 1, wherein said extraction is carried out for a period of 5 to 360 minutes.
4. The process according to claim 1, wherein said aqueous solvent is water or a dilute alkaline solution of less than 1 N.

* * * * *